United States Patent
Alokaili et al.

(10) Patent No.: US 9,402,979 B2
(45) Date of Patent: Aug. 2, 2016

(54) RELEASABLE TORQUE DEVICE

(71) Applicants: KING ABDULLAH INTERNATIONAL MEDICAL RESEARCH CENTER, Riyadh (SA); KING SAUD BIN ABDULAZIZ UNIVERSITY FOR HEALTH SCIENCES, Riyadh (SA); NATIONAL GUARD HEALTH AFFAIRS, Riyadh (SA)

(72) Inventors: Riyadh Nasser Alokaili, Riyadh (SA); Asma Matar Alenezi, Riyadh (SA)

(73) Assignees: KING ABDULLAH INTERNATIONAL MEDICAL RESEARCH CENTER, Riyadh (SA); KING SAUD BIN ABDULAZIZ UNIVERSITY FOR HEALTH SCIENCES, Riyadh (SA); NATIONAL GUARD HEALTH AFFAIRS, Riyadh (SA)

( * ) Notice: Subject to any disclaimer, the term of this patent is extended or adjusted under 35 U.S.C. 154(b) by 102 days.

(21) Appl. No.: 14/328,577

(22) Filed: Jul. 10, 2014

(65) Prior Publication Data
US 2016/0008587 A1  Jan. 14, 2016

(51) Int. Cl.
*A61M 25/09* (2006.01)

(52) U.S. Cl.
CPC .................. *A61M 25/09041* (2013.01); *A61M 2025/09116* (2013.01)

(58) Field of Classification Search
CPC ............. A61M 25/09041; A61M 2025/09116; A61M 2025/09125
See application file for complete search history.

(56) References Cited

U.S. PATENT DOCUMENTS

| | | | | |
|---|---|---|---|---|
| 4,726,369 A * | 2/1988 | Mar | ................ | A61M 25/09041 600/434 |
| 5,137,288 A * | 8/1992 | Starkey | ................ | A61M 25/09 279/42 |
| 5,137,517 A * | 8/1992 | Loney | ................ | A61M 25/013 24/115 M |
| 5,161,534 A * | 11/1992 | Berthiaume | .......... | A61M 25/01 226/127 |
| 5,219,332 A * | 6/1993 | Nelson | ................... | A61B 17/22 600/434 |
| 5,325,746 A * | 7/1994 | Anderson | ............. | A61B 17/22 24/115 M |
| 5,325,868 A * | 7/1994 | Kimmelstiel | .......... | A61B 17/22 600/585 |
| 5,392,778 A * | 2/1995 | Horzewski | ...... | A61M 25/09041 600/434 |
| 6,030,349 A * | 2/2000 | Wilson | ............ | A61M 25/09041 600/434 |

(Continued)

*Primary Examiner* — Adam J Eiseman
(74) *Attorney, Agent, or Firm* — Richard C. Litman

(57) ABSTRACT

The releasable torque device obviates the need for removal of the wire introducer in order to torque or manipulate a vascular or other guide wire and/or catheter in a medical procedure, and further obviates the need to remove the torque device for wire and/or catheter introduction. The device may include a base cylinder and an inflation cylinder defining a variable fluid volume therebetween. As the inflation cylinder is pushed toward the base cylinder, the fluid is forced through a port in the inner wall of the inflation cylinder and between a tubular inner cylinder and an inflatable guide wire grip within the inner cylinder to squeeze the grip onto the guide wire passing axially therethrough. Alternatively, the device only has a central tube and an inflatable guide wire grip therein, using a remotely disposed fluid pump and reservoir supplying fluid to the tube and guide wire grip.

11 Claims, 5 Drawing Sheets

(56) References Cited

U.S. PATENT DOCUMENTS

| | | | |
|---|---|---|---|
| 6,834,842 B2 | 12/2004 | Houde | |
| 8,496,603 B2* | 7/2013 | Mamourian | A61M 25/09041 600/434 |
| 8,518,011 B2 | 8/2013 | Goodson, IV et al. | |
| 2003/0225395 A1* | 12/2003 | Griffis | A61M 25/09 604/528 |
| 2005/0070820 A1* | 3/2005 | Boutillette | A61M 25/09041 600/585 |
| 2005/0085746 A1 | 4/2005 | Adams et al. | |
| 2007/0004991 A1* | 1/2007 | Shelton | A61M 25/0113 600/585 |
| 2007/0118079 A1* | 5/2007 | Moberg | A61F 2/95 604/164.07 |
| 2011/0276115 A1 | 11/2011 | Merrill | |
| 2012/0253318 A1 | 10/2012 | Kimura | |
| 2013/0261388 A1 | 10/2013 | Jenkins et al. | |
| 2014/0171914 A1* | 6/2014 | Rowe | A61M 25/02 604/510 |

* cited by examiner

RELEASABLE TORQUE DEVICE

BACKGROUND OF THE INVENTION

1. Field of the Invention

The present invention relates generally to medical devices and instruments, and particularly to a releasable torque device that selectively grips and releases a guide wire passing through the device to provide for both introduction and torsional manipulation of the guide wire.

2. Description of the Related Art

Guide wires are frequently used in various endovascular surgical fields to guide and position a catheter, stent, or other tubular device (lumen) in the body of a patient. These guide wires must be manipulated as they are passed through the vascular, urinary, or other system in the body, in order to position the distal end of the guide wire (and thus the catheter or other lumen) properly in the body. This is generally done by twisting or torqueing the guide wire to steer it through the vascular system as desired.

Guide wires are generally introduced into a catheter and into the body by a device known as an introducer. The conventional introducer is a separate component from the torque device used to torque or steer the guide wire and catheter. Conventional torque devices must be removed from the guide wire and catheter in order for the introducer to be used, and the introducer must be removed from the guide wire and catheter assembly in order for the torque device to be secured to the guide wire and/or catheter for their manipulation.

Thus, a releasable torque device solving the aforementioned problems is desired.

SUMMARY OF THE INVENTION

The releasable torque device is a rigid tubular component having an elongate, cylindrical, selectively inflatable guide wire grip therein. The rigid tube and guide wire grip together define an axially elongate toroidal configuration. The guide wire grip may be selectively expanded inside the surrounding tube to squeeze the guide wire grip onto a guide wire inserted through the axially open center of the guide wire grip, thereby permitting the guide wire to be torqued by rotating the releasable torque device.

In one embodiment, the releasable torque device includes a base cylinder, the wall of the cylinder having an annular slot formed therein that extends axially for a portion of the length of the cylinder. An inflation cylinder has parallel and coaxial cylindrical walls and an annular closed end between the coaxial walls, the outer cylindrical wall fitting closely within and sliding telescopically in the slot defined in the base cylinder. The inner cylindrical wall of the inflation cylinder is the rigid tube surrounding the inflatable guide wire grip. The inner cylindrical wall has a port defined therein, permitting fluid flow through the inner cylindrical wall to inflate the guide wire grip. As the inflation cylinder is pushed toward the base cylinder, the volume of space between the two coaxial walls and annular closed end of the inflation cylinder is compressed by the base cylinder, forcing any fluid therein through the port to inflate the inflatable guide wire grip. This squeezes the guide wire grip onto the guide wire to permit the guide wire to be torqued by rotating the introducer.

Another embodiment dispenses with the base cylinder and inflation cylinder, leaving only the rigid tube having the inflatable guide wire grip therein. A remotely located fluid pump and reservoir is actuated to supply fluid pressure to the volume between the tube and the guide wire grip for operation of the device.

The guide wire grip may have a high friction guide wire contact surface to enhance the clamping action of the guide wire grip on the guide wire. Also, instead of surrounding the guide wire, the guide wire grip may subtend only a portion of the inner wall of the surrounding tube, clamping the guide wire against the wall of the tube when inflated. These various embodiments may be combined in any practicable manner as desired.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The releasable torque device provides for the manipulation of a catheter guide wire without need to remove the introducer to apply a separate guide wire torqueing device. Various embodiments are described herein.

Figure 1A:
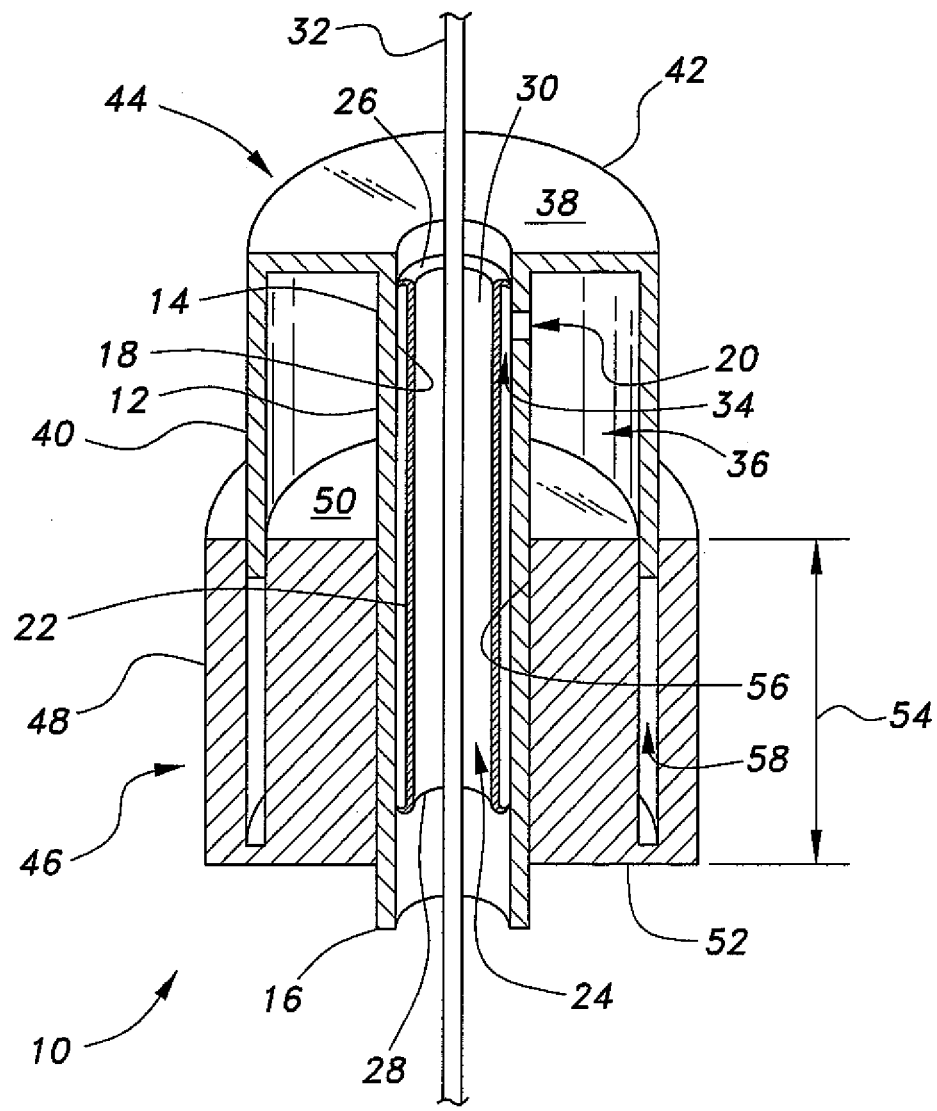
FIG. 1A is an enlarged environmental perspective view in section of a releasable torque device according to the present invention, shown with a guide wire freely passing therethrough, the grip being deflated.
Figure 1B:
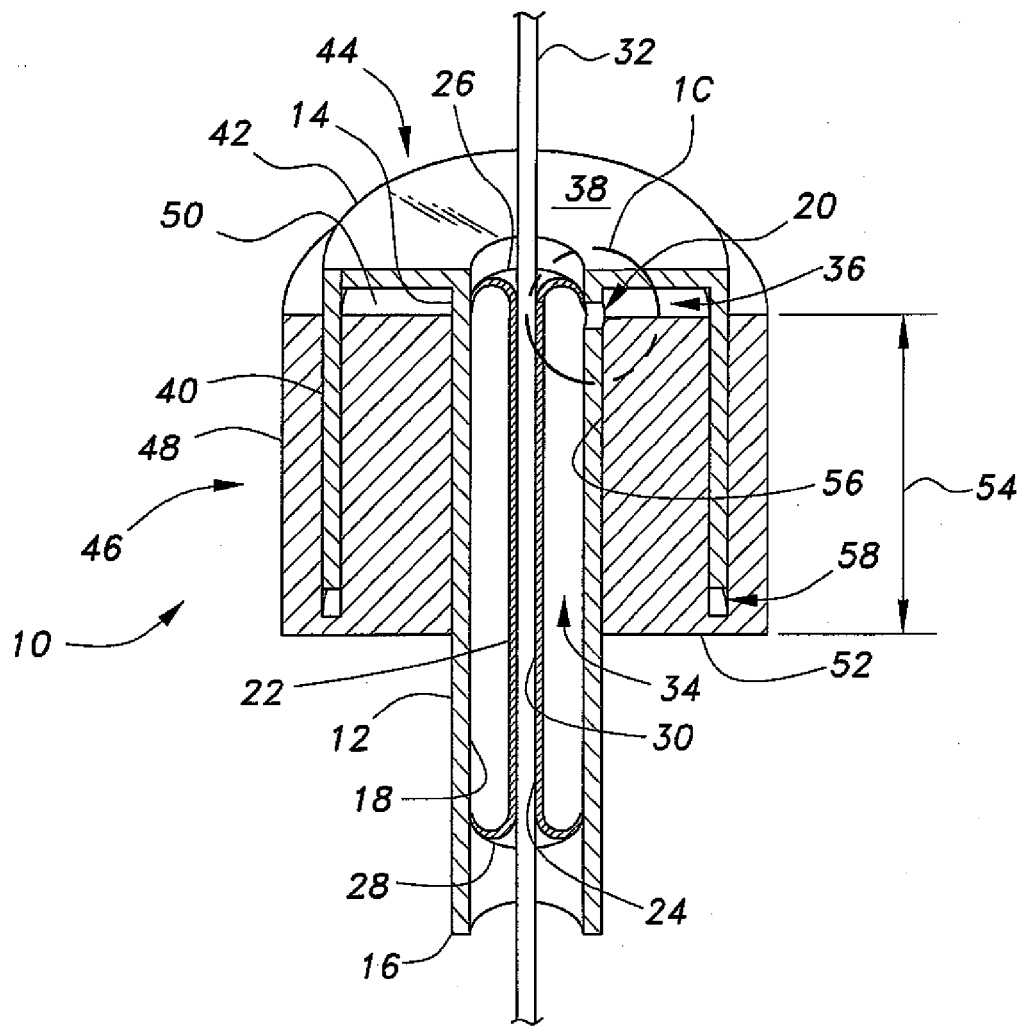
FIG. 1B is an enlarged environmental perspective view in section of the releasable torque device of FIG. 1A, showing the grip inflated to clamp the guide wire for manipulation thereof.

FIGS. 1A and 1B of the drawings illustrate two different operative states for a releasable torque device 10, hereinafter referred to as "device 10." It will be understood that the device 10, as shown in FIGS. 1A and 1B, is greatly enlarged for clarity in the drawings. The device 10 comprises an elongate rigid central tube 12 having a first end 14, an opposite second end 16, and an inner surface 18 (the tube 12 is "rigid" in the sense that it is made from an inflexible material; the tube 12 may be slidably disposed as part of an assembly). An inflation port 20 is defined in the wall of the tube 12 adjacent its first end 14, the function of the inflation port 20 being described further below.

Figure 1C:
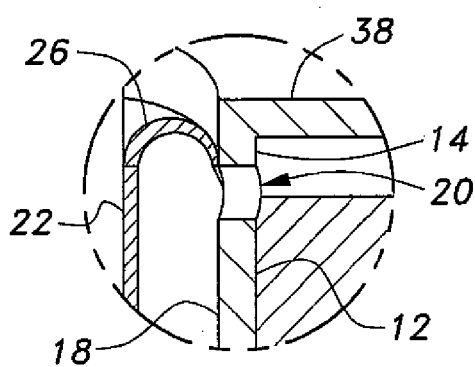
FIG. 1C is a detail view of area 1C of FIG. 1B.

An elongate, tubular, inflatable guide wire grip 22 is installed concentrically within the rigid central tube 12, forming an inner liner that subtends substantially the entire inner surface 18 of the tube 12. The guide wire grip 22 has an elongate toroid configuration when inflated, defining an axially open guide wire passage 24 that extends completely through the length of the guide wire grip 22 and the surrounding rigid tube 12. The guide wire grip 22 has mutually opposed first and second ends 26 and 28 that are sealed to the inner wall 18 of the rigid tube 12 at the respective first and second ends 14 and 16 thereof. FIG. 1C is a detail view showing attachment of the first end 26 of the guide wire grip to the inner wall or surface 18 of the rigid tube. The guide wire grip 22 is formed of a suitable elastomeric material, such as the material used in the manufacture of balloons used in vascular medical procedures. The guide wire grip 22 includes a guide wire contact surface 30, which preferably has sufficient friction to grip a guide wire 32 removably disposed through the center of the rigid tube 12 and the guide wire grip 22. The guide wire grip 22 and the surrounding tube 12 are of substantially identical configurations in FIGS. 1A, 1B, 1C, 2, and 4. An alternative guide wire grip configuration is shown in FIG. 3, discussed below.

The guide wire grip 22 and the surrounding rigid tube 12 define a toroidal, variable volume guide wire grip inflation chamber 34 therebetween. In FIG. 1A the inflation chamber 34 is shown in its minimal volume state, thus allowing the elastomer grip 22 to relax outward toward the inner surface 18 of the rigid tube 12. This maximizes the diameter of the guide wire passage 24 through the grip 22, thus allowing the guide wire 32 to be inserted, withdrawn, and/or otherwise manipulated independently of the device 10. When a fluid (e.g., air or other gas, or liquid) is passed through the inflation port 20 of the tube 12, the fluid causes the inflation chamber 34 to expand, generally as shown in FIG. 1B, thereby forcing the guide wire grip 22 radially inward due to the inelasticity of the rigid tube 12. The inward movement of the guide wire grip 22 results in the guide wire contact surface 30 of the grip 22 contacting the guide wire 32 (if installed). This eliminates any chance of relative movement between the guide wire 32 and surrounding guide wire grip 22, clamping the guide wire 32 in the guide wire grip 22 and allowing the practitioner to manipulate the guide wire 32 by maneuvering the device 10, whether by pushing, pulling, or twisting movement.

In the embodiments of FIGS. 1A through 3, the variable volume master inflation chamber 36 comprises two components that concentrically surround the central tube 12 and its guide wire grip 22. The first end 14 of the rigid tube 12 has an annular end wall 38 that extends outward therefrom. A coaxial cylindrical outer wall 40 extends from the outer edge 42 of the end wall 38 parallel to the central tube 12. The central tube 12, end wall 38, and outer cylindrical wall 40 comprise an annular inflation cylinder 44.

A base cylinder 46 is coupled with the inflation cylinder 44. The base cylinder 46 has an outer surface 48 and mutually opposed first and second ends 50, 52 defining a base cylinder length 54. A coaxial passage 56 extends completely through the length of the base cylinder 46. The rigid tube 12 of the inflation cylinder 44 telescopes within the base cylinder passage 56. An annular slot 58 is formed coaxially in the base cylinder 46 between the outer surface 48 and the passage 56. The slot 58 extends from the first end 50 for the substantial majority of the length 54 of the base cylinder 46 to a depth short of the second end 52 of the base cylinder 46, i.e., the slot 58 is "blind" and does not extend completely through the entire length 54 of the base cylinder 46. The outer wall 40 of the inflation cylinder 44 telescopes within the slot 58 of the base cylinder 46. The rigid tube 12, end wall 38, and outer wall 40 of the inflation chamber 44, and the first end 50 of the base cylinder 44 define the master inflation chamber 36.

It will be seen that as the inflation cylinder 44 telescopes relative to the base cylinder 46, the volume of the master inflation chamber 36 will vary. When the inflation cylinder 44 is pushed toward the base cylinder 46, as shown in FIG. 1B, the internal volume of the master inflation chamber 36 is reduced. This causes any working fluid therein (liquid, air or other gas, etc.) to be forced from the master inflation chamber 36 through the inflation port 20 into the guide wire grip inflation chamber 34. The fluid flowing into the guide wire grip inflation chamber 34 causes the elastomer guide wire grip 22 to distend radially inward to the central axis of the rigid tube 12 due to the rigidity of the tube 12 in which the guide wire grip 22 is installed. This results in the guide wire contact or gripping surface 30 being forced into contact with the guide wire 32, as shown in FIG. 1B, thus clamping or gripping the guide wire 32 within the device 10 to allow the guide wire 32 to be maneuvered by manipulating the device 10. When the inflation cylinder 44 is pulled away from the base cylinder 46, the volume of the master inflation chamber 36 will expand and the elastomeric nature of the guide wire grip 22 causes the grip to contract against the wall of the rigid tube 12 so that when the inflation cylinder 36 is pulled out far enough, the device reverts to the configuration of FIG. 1A.

Figure 2:
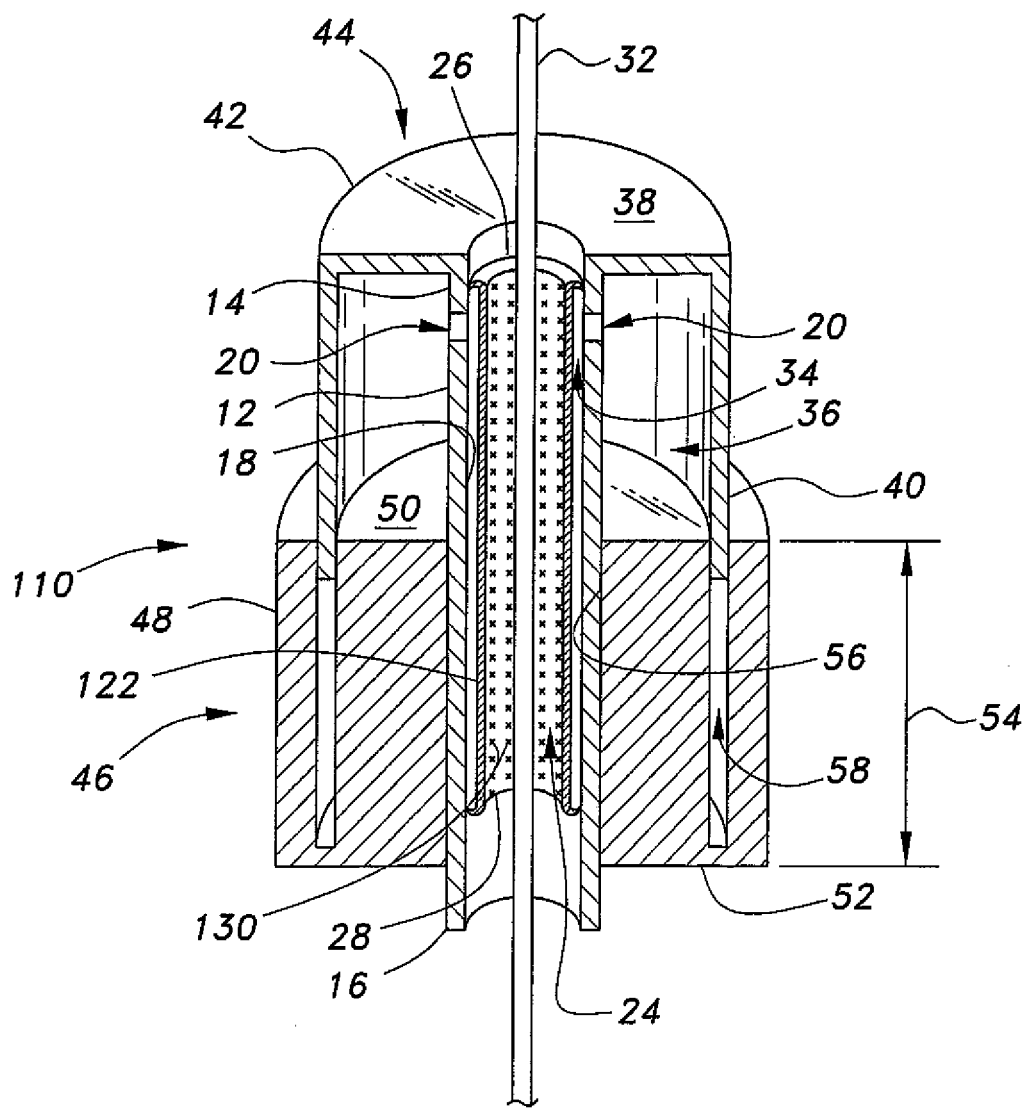
FIG. 2 is an enlarged environmental perspective view in section of the releasable torque device of FIG. 1, wherein the inwardly facing surface of the guide wire grip is provided with a high friction surface and an optional second inflation port.
Figure 3:
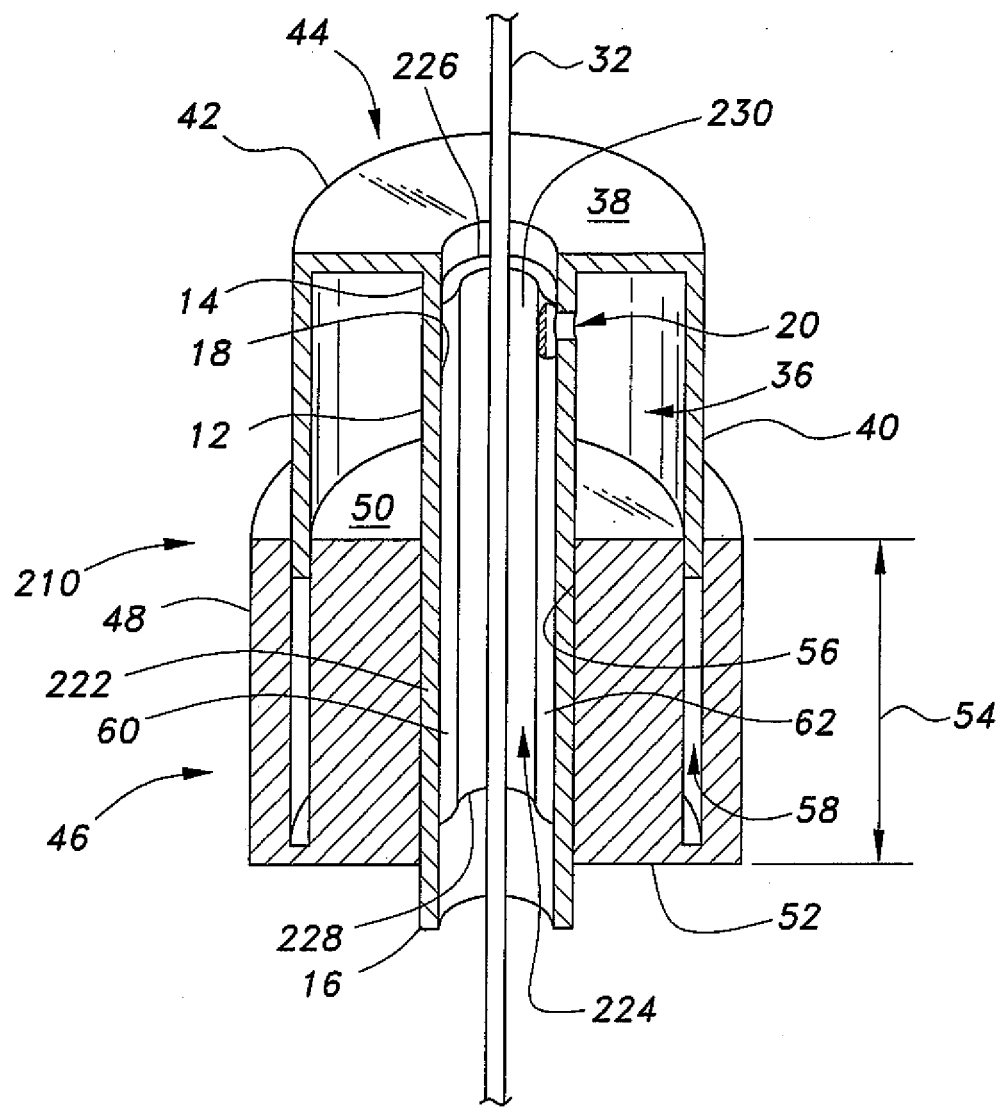
FIG. 3 is an enlarged environmental perspective view in section of an alternative embodiment of a releasable torque device according to the present invention, wherein the guide wire grip subtends only a portion of the inner wall of the central passage.

FIG. 2 shows a modification of the device 10 illustrated in FIGS. 1A through 1C. The device 110 of FIG. 2 is configured nearly identically to the device 10 of FIGS. 1A and 1B with correspondingly numbered components, the primary exception being the guide wire contact surface of the guide wire grip. In FIG. 2, the guide wire grip is designated by the reference numeral 122, as it differs from the corresponding component 22 of FIGS. 1A and 1B by having a different guide wire contact surface (130, in FIG. 2, as opposed to the surface 30 of the device 10 of FIGS. 1A and 1B). The guide wire contact surface 130 has a high friction coefficient surface, provided by a large number of small protuberances. These protuberances may be formed of the same material as the guide wire grip 122, i.e., a relatively soft and resilient rubberized or plastic material, or may comprise harder, tooth-like structures projecting inwardly toward the guide wire 32. (Alternatively, the surface 30 of the device of FIGS. 1A-1C may be coated with or comprise a material having a high coefficient of friction.) When the guide wire grip 122 is inflated to grip the guide wire 32, as described above, the high friction surface 130 provides enhanced grip of the guide wire 32 to further limit or preclude any slippage between the high friction gripping surface 130 and the guide wire 32. It will also be noted that two inflation ports 20 are provided in the device 110 of FIG. 2, an option that may also be provided with the device 10 of FIGS. 1A through 1C.

FIG. 3 of the drawings illustrates another slightly different embodiment from the device 10 of FIGS. 1A and 1B, and the device 110 of FIG. 2. The device 210 of FIG. 3 is configured nearly identically to the devices 10 of FIGS. 1A and 1B and 110 of FIG. 2 with correspondingly numbered components, the exception being the configuration of the guide wire grip. In the device 210 of FIG. 3, the guide wire grip 222 does not have a completely cylindrical configuration, but rather has a crescent or C-shaped cross section and subtends only an arcuate portion of the inner surface 18 of the tube 12. The two opposed edges 60 and 62 limiting the arcuate extent of the grip 222 are shown clearly in the cross-sectional view of FIG. 3. Otherwise, the grip 222 extends axially through the tube 12 to a similar extent as the grips 22 and 122 in their respective embodiments. The grip 222 has a first end 226 at the first end 14 of the tube 12 and an opposite second end 228 at the second end 16 of the tube 12. The configuration of the grip 222 defines an open-sided guide wire passage 224 and semicylindrical guide wire gripping or contact surface 230 within the grip 222. While the guide wire grip 222 of FIG. 3 is shown subtending approximately 180° of the inner surface 18 of the tube 12, it will be seen that the guide wire grip may be configured to extend about a greater or lesser circumferential expanse of the tube 12, as desired. It will also be noted that this semicircumferential guide wire grip 22 may be incorporated in any of the other embodiments of the device.

Figure 4:
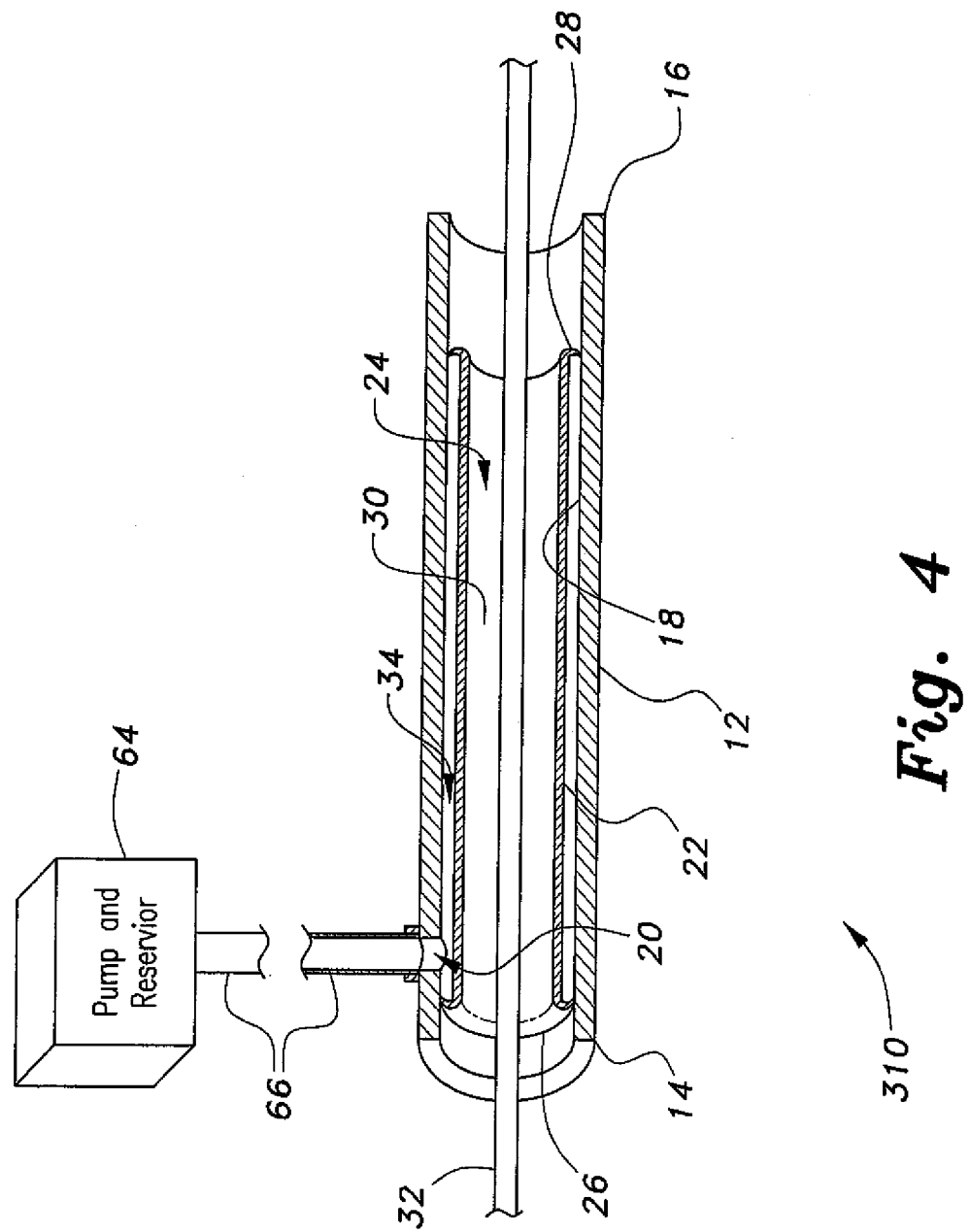
FIG. 4 is an enlarged environmental perspective view in section of another alternative embodiment of a releasable torque device according to the present invention, having a single rigid cylinder and an external inflation pump.

FIG. 4 illustrates an additional embodiment, designated as device 310. It will be seen that the device 310 of FIG. 4 is devoid of the base cylinder and most of the inflation cylinder components of other embodiments, generally comprising only the central rigid tube 12 and the internal tubular guide wire grip 22. The tube 12 and guide wire grip 22 define a guide wire grip inflation chamber 34, as described above. However, a separate, remotely located fluid pump and reservoir 64 define the master inflation chamber for the device 310 of FIG. 4. The pump and reservoir 64 communicate fluidly with the inflation port 20 of the tube 12 by a fluid transfer line 66. The fluid pump and reservoir 64 are shown only generally in FIG. 4, as they may be conventional small devices, as used in the medical and other fields, e.g., aquarium pumps, etc.

It is to be understood that the present invention is not limited to the embodiments described above, but encompasses any and all embodiments within the scope of the following claims.

We claim:

1. A releasable torque device, comprising:
an elongate rigid tube having a first end, a second end opposite the first end, an inner surface, and at least one inflation port defined therein adjacent the first end;
an annular end wall extending outward from the first end of the rigid tube, the end wall having an outer edge;
an outer wall extending from the outer edge of the end wall parallel to the rigid tube, the rigid tube, the end wall, and the outer wall defining an annular inflation cylinder;
a selectively operable, variable volume master inflation chamber, the at least one inflation port fluidly connecting the master inflation chamber with the guide wire grip inflation chamber;
an elongate, selectively inflatable guide wire grip disposed within the rigid tube, the guide wire grip having a first end sealed to the inner surface of the rigid tube at the first end, a second end sealed to the inner surface of the rigid tube at the second end, an inward facing guide wire contact surface, the rigid tube and the guide wire grip defining a selectively variable guide wire grip inflation chamber therebetween, the rigid tube defining an axially open guide wire passage extending through the tube; and
a base cylinder having:
an outer surface;
a first end and a second end opposite the first end, the first end and the second end of the base cylinder defining a base cylinder length;
a central axial passage extending completely through the length of the base cylinder; and
an annular slot disposed between the outer surface and the central axial passage of the base cylinder, the slot extending from the first end of the base cylinder substantially the majority of the length of the base cylinder, the rigid tube being slidably and telescopically disposed within the central axial passage, the outer wall of the inflation cylinder being slidably and telescopically disposed within the annular slot of the base cylinder;
wherein the rigid tube, the end wall, the outer wall of the inflation cylinder and the first end of the base cylinder define the master inflation chamber.

2. The releasable torque device according to claim 1, wherein the guide wire contact surface has a coefficient of friction providing enhanced grip of a guide wire.

3. The releasable torque device according to claim 1, wherein the guide wire grip has an elongate toroidal configuration and subtends the entirety of the inner surface of the rigid tube, the guide wire grip being adapted for surrounding the guide wire extending through the guide wire passage and clamping the guide wire when the guide wire grip inflation chamber is fully inflated, whereby the rigid tube may be rotated to apply torque to the guide wire.

4. The releasable torque device according to claim 2, wherein the guide wire contact surface enhanced gripping includes protuberances about the contact surface.

5. The releasable torque device according to claim 1, wherein the guide wire grip is elastomeric.

6. The releasable torque device according to claim 1, further comprising a guide wire selectively extending through the guide wire passage.

7. A releasable torque device, comprising:
an elongate rigid tube having a first end, a second end opposite the first end, an inner surface, and at least one inflation port defined therein adjacent the first end, the rigid tube defining an axially open guide wire passage extending through the tube;
an annular end wall extending outward from the first end of the rigid tube, the end wall having an outer edge;
an outer wall extending from the outer edge of the end wall parallel to the rigid tube, the rigid tube, the end wall, and the outer wall defining an annular inflation cylinder;
a base cylinder having an outer surface, a first end, a second end opposite the first end, the first end and the second end of the base cylinder defining a base cylinder length, a central axial passage formed completely through the length of the base cylinder, and an annular slot disposed between the outer surface and the central axial passage of the base cylinder, the slot extending from the first end of the base cylinder substantially the majority of the length of the base cylinder, the rigid tube being slidably and telescopically disposed within the central axial passage, the outer wall of the inflation cylinder being slidably and telescopically disposed within the annular slot of the base cylinder, the rigid tube, the end wall, and the outer wall of the inflation cylinder and the first end of the base cylinder defining a master inflation chamber; and
an elongate, tubular, selectively inflatable guide wire grip disposed within the rigid tube, the guide wire grip having a first end sealed to the inner surface within the first end of the rigid tube, a second end sealed to the inner surface within the second end of the rigid tube, the guide wire grip having an inward facing guide wire contact surface, the rigid tube and the guide wire grip defining a selectively variable volume guide wire grip inflation chamber therebetween, the port in the rigid tube fluidly connecting the master inflation chamber and the guide wire grip inflation chamber.

8. The releasable torque device according to claim 7, wherein the guide wire grip has an elongate toroidal configuration and subtends the entirety of the inner surface of the rigid tube, the guide wire grip being adapted for surrounding a guide wire extending through the guide wire passage and clamping the guide wire when the guide wire grip inflation chamber is fully inflated, whereby the rigid tube may be rotated to apply torque to the guide wire.

9. The releasable torque device according to claim 7, wherein the guide wire contact surface has a coefficient of friction providing enhanced grip of a guide wire with the contact surface, wherein the guide wire contact surface enhanced gripping includes protuberances about the contact surface.

10. The releasable torque device according to claim 7, wherein the guide wire grip is elastomeric.

11. The releasable torque device according to claim 7, further comprising a guide wire selectively extending through the guide wire passage.

* * * * *